(12) United States Patent
Raymond et al.

(10) Patent No.: US 7,075,565 B1
(45) Date of Patent: Jul. 11, 2006

(54) OPTICAL INSPECTION SYSTEM

(75) Inventors: Douglas W. Raymond, Orinda, CA (US); Richard D. Fleming, Walnut Creek, CA (US)

(73) Assignee: Landrex Technologies Co., Ltd., Taipei-Hsien (TW)

( * ) Notice: Subject to any disclaimer, the term of this patent is extended or adjusted under 35 U.S.C. 154(b) by 737 days.

(21) Appl. No.: 09/593,352

(22) Filed: Jun. 14, 2000

(51) Int. Cl.
*H04N 7/18* (2006.01)

(52) U.S. Cl. .................. 348/126; 348/87; 348/131

(58) Field of Classification Search ........... 348/126, 348/87, 132, 131, 61; 710/22, 27; 712/35; 382/154
See application file for complete search history.

(56) References Cited

U.S. PATENT DOCUMENTS

| | | | | |
|---|---|---|---|---|
| 4,896,211 | A | * | 1/1990 | Hunt et al. .................. 348/132 |
| 5,060,065 | A | | 10/1991 | Wasserman |
| 5,245,421 | A | * | 9/1993 | Robertson et al. .......... 348/126 |
| 5,260,779 | A | * | 11/1993 | Wasserman .................. 348/87 |
| 5,517,234 | A | | 5/1996 | Gerber et al. |
| 5,550,583 | A | | 8/1996 | Amir et al. |
| 5,974,480 | A | * | 10/1999 | Qureshi et al. ................ 710/27 |
| 6,064,759 | A | * | 5/2000 | Buckley et al. ............. 382/154 |
| 6,256,724 | B1 | * | 7/2001 | Hocevar et al. .............. 712/35 |
| 6,260,081 | B1 | * | 7/2001 | Magro et al. .................. 710/22 |

FOREIGN PATENT DOCUMENTS

EP    0 772 381 A1 *   5/1997

OTHER PUBLICATIONS

John C. Russ, "The Image Processing Handbook-3rd Edition", CRS Press-IEEE Press, 1999, 5 pgs.

* cited by examiner

*Primary Examiner*—Allen Wong
(74) *Attorney, Agent, or Firm*—MacPherson Kwok Chen & Heid LLP (57) ABSTRACT

An automated optical inspection system includes a plurality of asynchronously triggerable cameras for providing image data of an object, such as a printed circuit board. The circuit board is divided into fields of view that are to be imaged in one or more cameras in one or more lighting modes. Each location on the board can be imaged by each camera in a plurality of lighting modes in a single pass across the board. The image data for each of the cameras can be concurrently transferred directly to main memory for opportunistic analysis by the main computer. The system allows the full bandwidth of the cameras to be utilized for reducing the inspection time of the board.

20 Claims, 7 Drawing Sheets

OPTICAL INSPECTION SYSTEM

CROSS REFERENCE TO RELATED APPLICATIONS

Not Applicable.

STATEMENT REGARDING FEDERALLY SPONSORED RESEARCH

Not Applicable.

FIELD OF THE INVENTION

The present invention relates generally to inspection systems, and more particularly, to automated optical inspection systems.

BACKGROUND OF THE INVENTION

Automated optical inspection (AOI) systems are used to inspect objects, such as printed circuit boards (PCBs), for a variety of defects. The system can inspect a PCB for proper component presence and orientation, proper solder joint formation, and solder bridges. In one optical inspection application, a system can inspect the toe fillet solder joints of a quad flat pack (QFP) integrated circuit. Such a package has four edges with leads protruding from each edge. Each lead is connected to a pad on the PCB by a solder joint. An incorrectly formed solder fillet will have an appearance that can be detected using well-known image processing algorithms.

Such an AOI system includes a camera head that shuttles back and forth relative to the PCB. The camera head includes an illumination system and a plurality of cameras. The illumination system may be provided, for example, as one or more light emitting diodes (LEDs), which provides lighting for the purpose of highlighting certain surfaces on the PCB and darkening other surfaces on the PCB to allow the cameras to capture images that are amenable to image processing analysis. Typically, the lights are normally turned off and are turned on only when the camera head is directly over a region or zone of interest on the PCB. Thus, the illumination system operates as a strobe light. With this strobe light approach, it is not necessary for the camera head to stop in order to acquire an image.

Each camera in the camera head captures a useful image of a particular zone of interest only when the light is on. Moreover, depending upon the particular region of interest over which the camera head is disposed, the illumination system operates in a particular lighting mode meaning that the illumination system provides light from particular ones of the LEDs (rather than from all of the LEDs). The lighting mode is selected to enhance the highlighting and darkening of the PCB regions and facilitate the image processing analysis. Thus the illumination system operates in a series of lighting modes during which particular cameras are able to capture images in a particular zone of interest.

Typically, the board being inspected is divided into stripes. Each stripe corresponds to a shuttle path along which the camera head travels. Each stripe is divided into fields of view (FOVs). As the camera head shuttles across various portions of the board, the illumination system strobes the lights in accordance with predetermined lighting modes to produce a flow of images from the cameras in the camera head. The images are transferred to memory via framegrabbers for analysis.

One conventional method of inspecting solder fillets is disclosed in U.S. Pat. No. 5,245,421, which discloses illuminating the fillet from its sides while a camera also views the fillet from the side to capture an image along an axial dimension of the fillet. Such a lighting technique or mode produces a view of the fillet in which the edges of the fillet appear light and the center of the fillet appears dark. The picture of the fillet is commonly referred to as having "snake eyes" or "cheeks" because a transect across it is light, then dark, then light again. A defective fillet will typically have low contrast. For example, a joint with inadequate solder will have no curvature and will look more uniformly dark. A joint with excess solder will also have low curvature and will also look more uniformly dark.

Generally, the inspection program in conventional AOI systems defines a series or pattern of paths, e.g., stripes, along the PCB being inspected. The camera head shuttles in a predetermined pattern along the stripes. The position of each of the cameras in the camera head relative to the PCB changes each time the camera head moves. Thus, components on the PCB do not appear in consistent positions in fields of camera view. A given field of view may, therefore, contain fillets of multiple orientations. For example, when the camera head is in one stripe, a given view may contain the upper left corner of one QFP and the lower right corner of another QFP. In another view, however, four QFPs may converge so that there are corners of four separate QFPs in the view. Some leads would be pointing east, others south, others west, and others north.

A lighting mode which lights the scene from north and south would produce the desired snake eyes pattern on both east-pointing and west-pointing leads, but would not produce the snake eyes pattern in the north-pointing and south-pointing leads. One lighting mode is thus unable to properly illuminate all four sets of toe fillets.

A second frame would have to be taken with an east-west lighting mode, to produce the snake eyes image on the north-pointing and south-pointing toe fillets. This arrangement requires that the camera head pass over the PCB for each lighting mode that is needed to inspect a given point on the board. Each pass over the board requires a significant amount of time. Since inspection systems are often a production process bottleneck, each additional pass is thus significant.

U.S. Pat. No. 5,260,779, assigned to the assignee of the present invention, attempts to reduce the inspection time of a PCB by taking pictures with two different lighting modes for each point of the circuit board. The system includes four angled cameras arranged in a symmetrical quartet, with all four cameras tilted thirty degrees from vertical. The optical axis of each camera is aligned to a common point in the plane of the circuit board to be inspected. The cameras are arranged in two opposing pairs such that the cameras in the first camera pair oppose each other in a direction perpendicular to the primary direction of motion of the camera head and the cameras in the second camera pair face each other in a direction which is parallel to the primary direction of motion. The cameras in the first pair operate in their odd video field while the cameras in the second pair operate in their even video field, and vice versa. The head velocity is controlled in such a way that each of the cameras takes one complete frame for every field of view of camera head motion.

The lighting system described in U.S. Pat. No. 5,260,779 supplies two flashes for each field of view's worth of motion along the board. One flash is for the first and second cameras which make up the first opposing pair and a second flash is for the third and fourth cameras which make up the second opposing pair. The camera head is required to visit a given point on the board once for each lighting mode/camera pair combination. Thus, there will be two visits if there are two lighting modes required for a camera. If there are three lighting modes for any camera, the camera head must visit the point three times, and so forth. In general, "n" passes over a field of view are required if "n" lighting modes are required for the inspection program.

A typical circuit board inspection program uses three to ten lighting modes, and therefore requires three to ten passes of the camera head relative to the circuit board. Each pass can take several seconds and thus in many automated assembly lines, the inspection machine is the slowest machine, and is therefore a process bottleneck.

A further disadvantage of known systems is the likelihood of losing image data due to the way the image data is captured and stored. Such optical inspection systems include a frame acquisition system having local memory and/or local processing. Thus, the main computer must access the image data over a bus, such as a PCI bus.

The overhead required of the processor to manage this process and the time required for the data transfer combine to significantly reduce the time available to analyze image data. For example, in a system where each camera has a dedicated processor, or a single dedicated memory, or both, the processor assigned to a particular heavily used camera may saturate well before the processors assigned to the other cameras saturate. In systems where a dedicated memory is assigned to each camera, it might be impossible to analyze all the windows in a given FOV before the camera begins to deliver image data for the next FOV. In order to receive incoming data from the next frame, the data being processed would be flushed to make room for the new incoming data or alternatively, the new data is simply written over the old data. In such a case, the old data is lost and the camera head would have to stop, or go back and retake the view later to regain the data. This leads to significant time delays in inspection time.

In addition, frame grabbing systems typically handle multiple cameras by multiplexing, but cannot handle them concurrently. For example, in the four camera system mentioned above, before camera two can be triggered, the entire image from camera one would have to be transmitted, and so forth. Thus, the full bandwidth of the cameras cannot be utilized.

It would, therefore, be desirable to provide an AOI system that triggers cameras asynchronously for allowing a point on an object under inspection to be imaged with multiple lighting modes in a single pass over the object. It would further be desirable for the optical processing system to include an image acquisition system that allows simultaneous transmission of image data from multiple cameras into main memory for opportunistic processing, which need not be completed prior to acquiring data from a subsequent stripe.

SUMMARY OF THE INVENTION

The present invention provides an automated optical inspection (AOI) system that minimizes the time required to inspect an object. While the invention is primarily shown and described in conjunction with inspecting printed circuit boards (PCBs), it is understood that the optical inspection system of the present invention can be utilized to inspect a wide variety of objects having detailed surface features.

In one aspect of the invention, an AOI system includes a main computer or processor that controls the overall operation of the AOI system, which can be done on a stripe-by-stripe basis. A plurality of asynchronously triggerable cameras can be coupled to a movable head assembly for positioning the cameras with respect to an object, such as a PCB. An illumination system, which can also form a part of the head assembly or can be separate from the head assembly, provides a plurality of lighting modes that illuminate the PCB for the cameras. A frame grabber unit receives the image data from the cameras and transmits the data to main memory that is directly accessible by the main computer.

In operation, the circuit board is divided into stripes and each stripe is further divided into one or more fields of view (FOV). The main computer can generate a view table for determining the locations within the stripes to be imaged, by which cameras, and in which lighting modes. The head assembly moves back and forth across the stripes at a constant velocity. The cameras image points on the board in multiple, desired lighting modes in a single pass. In one embodiment, each camera can image a given point on the circuit board twice with each image having a different lighting mode. The speed of the assembly can be selected to allow the board to be imaged with a predetermined number of lighting modes in one pass over each stripe. This arrangement allows the inspection time to be minimized by selecting optimal parameters for head speed and number of passes over the board based upon the number of lighting modes required for each point on the board.

In a further aspect of the invention, the frame grabber includes a plurality of direct memory access (DMA) channels for storing data in a memory which is directly accessible by the main computer. With this arrangement, images can be concurrently and rapidly transferred from an image acquisition board to the main memory for immediate storage and processing. Thus, data will not be flushed or overwritten.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
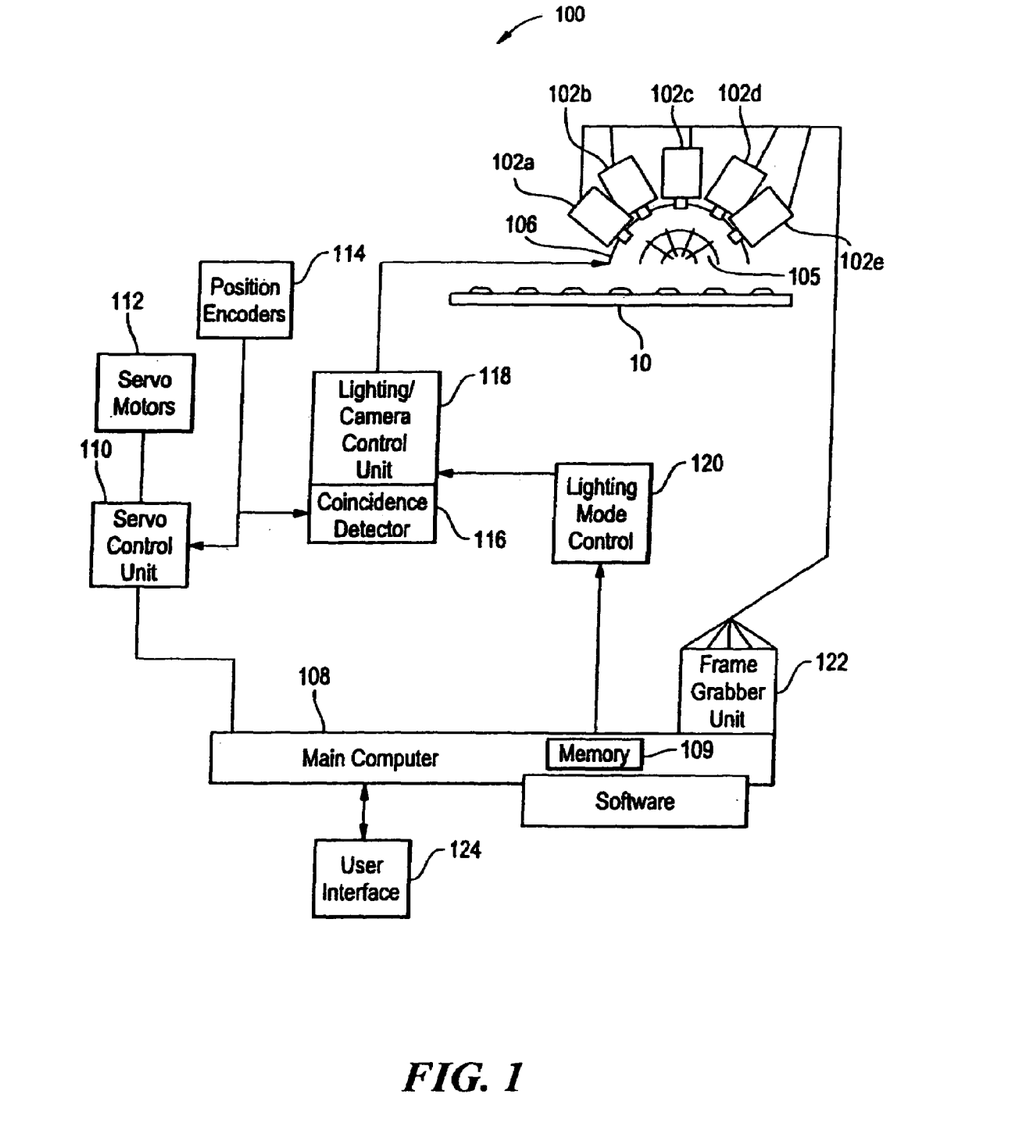
FIG. 1 is a schematic block diagram of an optical inspection system in accordance with the present invention.

FIG. 1 shows an exemplary embodiment of an automated optical inspection (AOI) system 100 in accordance with the present invention. In general, the system 100 utilizes a series of cameras 102a–e to optically inspect an object, such as a printed circuit board (PCB) 10.

Figure 1A:
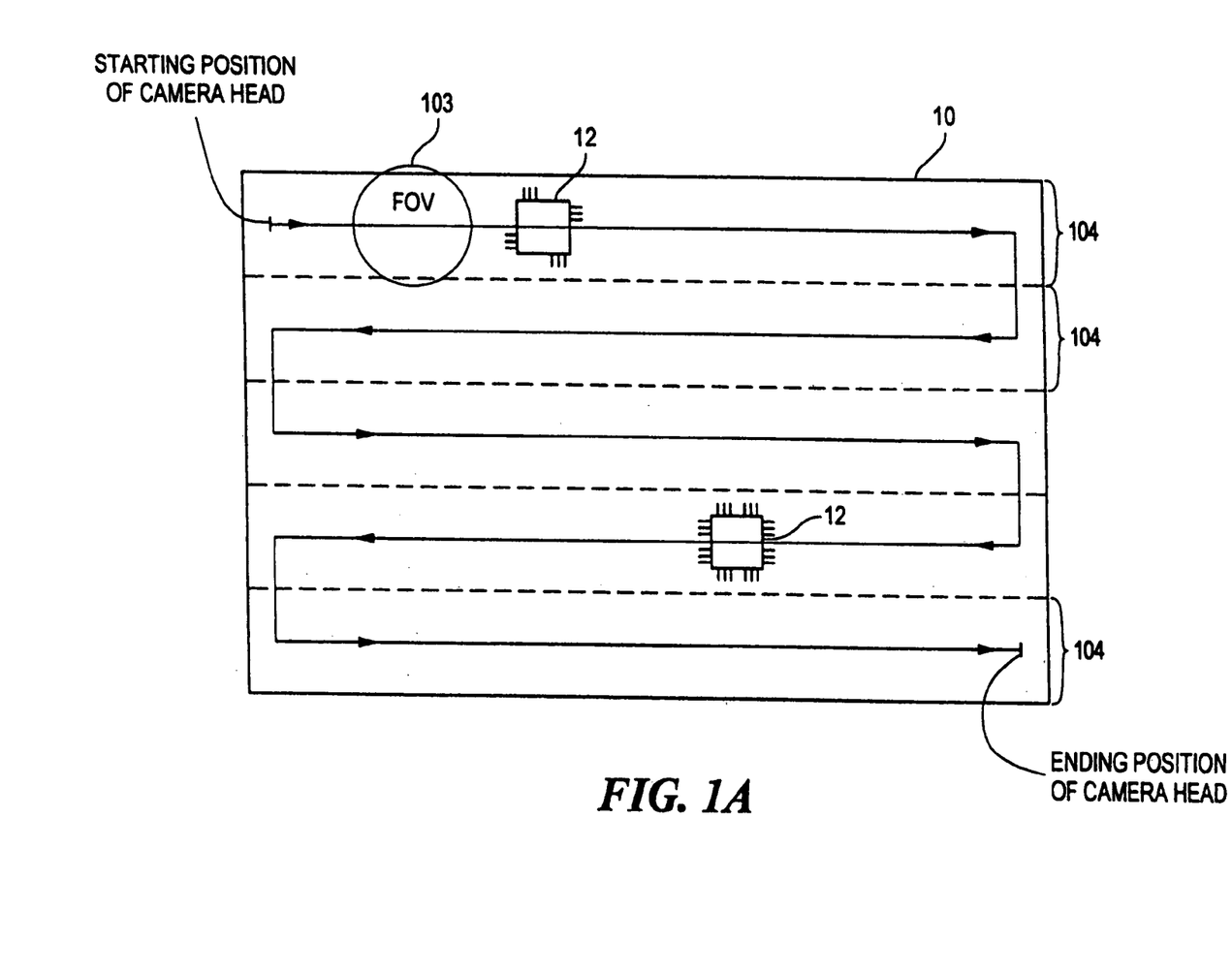
FIG. 1A is a schematic diagram which pictorially represents stripes over a printed circuit board for inspection by the optical inspection system of FIG. 1.

Referring briefly to FIG. 1A, the system 100 divides the PCB 10 into so-called stripes 104, which are subdivided into fields of view (FOVs) 103 that are analyzed to identify manufacturing defects associated with populating the PCB with circuit components 12, such as non-conforming solder joints. As known to one of ordinary skill in the art, the cameras move along the stripes to acquire the desired image data for the PCB. At any given time, each camera will have a predetermined FOV 103 corresponding to the position of the camera with respect to the PCB, as described more fully below. Since the inspection stations can be a bottleneck in a production environment, the decrease in board inspection time as compared with known optical inspection systems is a significant feature of the automated inspection system of the present invention.

Referring again to FIG. 1, the optical inspection system 100 includes a plurality of cameras 102a–102e for providing images of the printed circuit board 10. The cameras 102a–102e move along the stripes to image desired portions of the board. An illumination system 105, disposed about a dome-shaped assembly 106 illuminates the PCB 10 in a desired manner. In one particular embodiment, the illumination system 105 is comprised of a plurality of light emitting diodes (LEDs) arranged in a matrix disposed on the dome-shaped assembly 106. In an exemplary embodiment, five cameras 102a–e are used. Four of the cameras 102a, 102b, 102d and 102e are disposed at an angle, e.g. thirty degrees with respect to a normal to a surface circuit board 10, and the fifth camera 102c is located directly over (vertical) the circuit board 10. The cameras 102a–102e can be secured to the dome assembly 106, which is moved across stripes of the board.

While an exemplary embodiment of the invention moves the cameras 102a–102e and lighting system 105 with respect to the circuit board, one of ordinary skill in the art will readily appreciate that the board position can be manipulated in relation to the cameras without departing from the invention. In addition, each of the lighting system 105, the cameras 102a–102e, and the board 10 can be manipulated independently. Also, those of ordinary skill in the art will appreciate that, although the illumination system 105 is here described as provided from LEDs, any type of lamp can also be used provided that the lamp or matrix of lamps can be operated in a strobe light fashion and can provide the necessary lighting modes. It should also be appreciated that although five cameras are here shown, fewer or more than five cameras can be used. The particular number of cameras, as well as the positioning of the cameras to be used in any particular application, can be readily varied to acquire the desired image data from a board under inspection. For example, one alternative embodiment can include one or more vertical cameras.

In an exemplary embodiment, a main computer 108 controls the overall operation of the system 100 on a stripe-by-stripe basis. Field of view (FOVs) within the stripes are imaged by one or more of the cameras 102. Partitioning a circuit board into stripes and FOVs is well known to one of ordinary skill in the art. As is also known, an inspection program for the FOVs can be generated based upon the board characteristics, as described more fully below.

Based upon the inspection program, the main computer 108 provides commands to a servo control unit 110, which controls the servo motor 112, to effect positioning of the dome 106 over each stripe of the circuit board 10. In an exemplary embodiment, the dome 106 is moved over the stripe and the LEDs 105 are strobed to illuminate the board for a particular one of the cameras 102a–102e. The actual position of the dome assembly 106 is determined by a position encoder 114. In one embodiment, the encoder 114 includes a pick-off type system having a linear encoder that generates digital quadrature signals providing a resolution of about five millionths of a meter. The digital servo control unit 110 receives the digital encoder signals and provides the necessary motor drive signal corrections to properly position the dome assembly 106 across a stripe. Such positioning and tracking of the dome assembly 106 is well known to one of ordinary skill in the art.

A coincidence detector 116 receives dome position information from the position encoders 114. The coincidence detector 116 compares the encoder dome position information to a position provided by the computer 108 and stored in the event memory at which one or more of the cameras 102a–102e are to be fired. When the coincidence detector 116 detects a match, a lighting/camera control unit 118 is notified and fires one or more of the cameras 102a–102e and activates selected LEDs in accordance with predetermined lighting mode information contained in the lighting mode control unit 120.

The system 100 further includes a frame grabber unit 122 that receives image data from each of the cameras 102a–102e and stores the data in a memory 109, which can be directly accessed by the main computer 108, as described in detail below. In general, this arrangement allows the main computer 108 to opportunistically analyze the image data in the memory 109 without the data being lost because processing for the current stripe was not completed before subsequent stripe data is received, as can occur in conventional systems.

A user interface 124 coupled to and cooperative with the main computer 108 allows a user to implement a desired production scheme and also allows the user to manually run selected inspection programs for a circuit board that requires additional attention.

Figure 2:
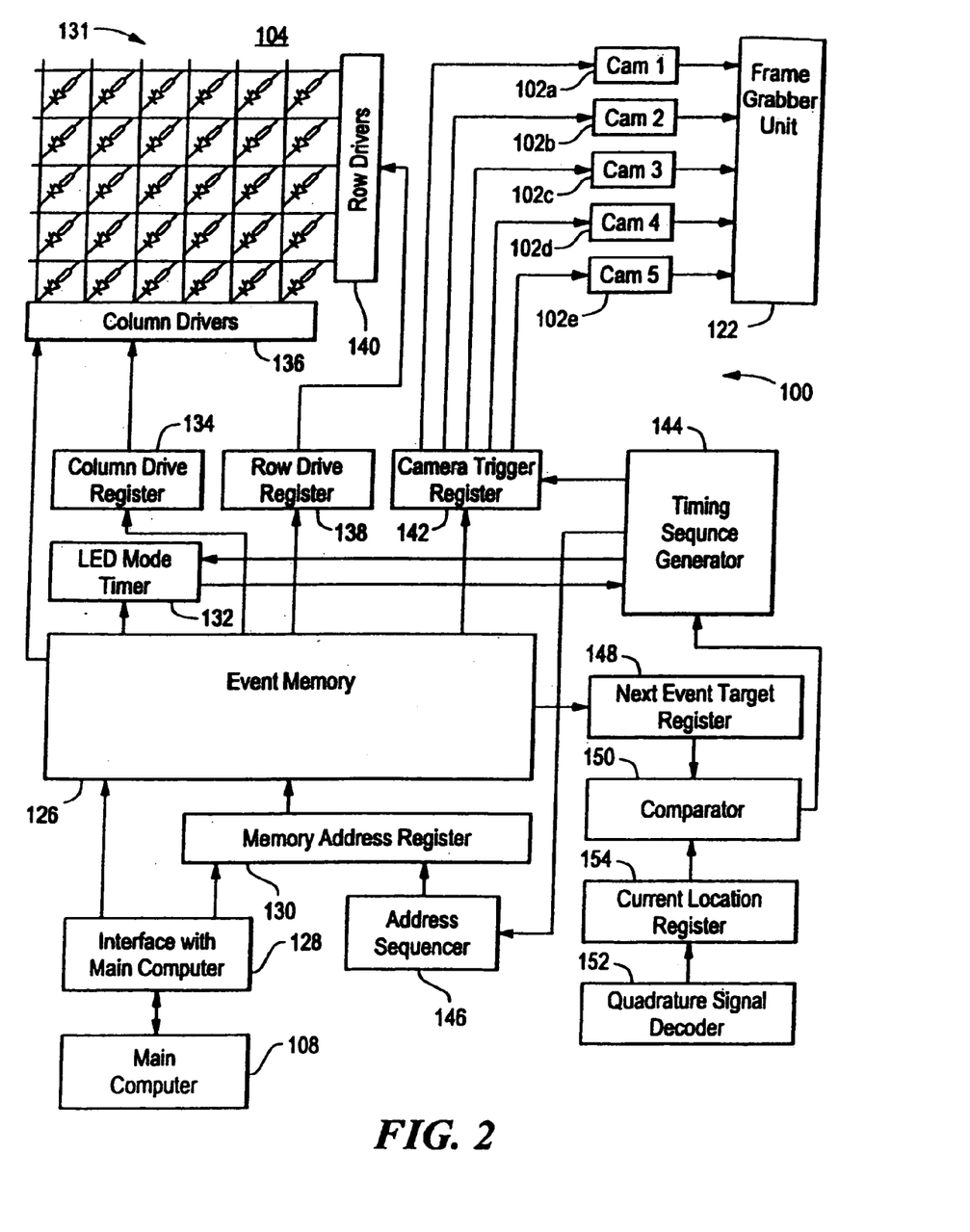
FIG. 2 is a more detailed block diagram of the optical inspection system of FIG. 1

FIG. 2 shows a more detailed implementation of the optical inspection system 100 of FIG. 1. The main computer 108 stores camera and lighting mode information into an event memory 126 on a stripe-by-stripe basis via an interface 128 and a memory address register 130. For a twenty-four inch board having 0.4 inch FOVs, the event memory 126 stores six hundred events, e.g., 24/0.04. Where the camera head has a slower speed, such as to image each point three times in a single pass, nine hundred events, e.g., 24/0.027, would be stored.

In an exemplary embodiment, each event memory location includes dome assembly position data, camera firing data, and lighting mode data. The event information is loaded into registers for controlling the cameras and lighting mode at each firing position. In one embodiment, the illumination assembly 105 is provided from a matrix of LEDs 131 and also includes an LED strobe timer 132. The strobe timer 132 can be provided as a sixteen bit timer which determines how long the LEDs 105 are active to control the brightness of the image. An LED column register 134 controls which column drivers 136 of an LED matrix are active and an LED row register 138 controls which row drivers 140 are active for a given event. In an exemplary embodiment, the LED matrix includes ten rows and forty columns spread about the dome 106 (FIG. 1). A camera trigger register 142 controls which cameras 102a–e fire for the event. It is understood that any number of cameras 102a–102e can be programmed to fire for each event. The cameras 102a–102e provide image data to the frame grabber unit 122.

A timing sequence generator 144 coordinates the timing of the camera triggering with the LEDs. In general, the camera(s) is triggered prior to a lighting cycle and terminates after the lighting cycle ends. After the event, an address sequencer 146 increments the memory address register 130, which then loads the next firing position location into a next event target register 148. A comparator 150 receives the next event location data and compares it to data from the dome position encoder 152 resident in the current dome position register 154. When the dome position register 154 value matches the next event target register 148 value, the comparator 150 provides an indication to the timing sequence generator 144, which triggers the appropriate camera 102 and LEDs 105.

The cameras 102 can be selected from a variety of cameras having suitable properties, such as speed, for imaging data and providing the data to main memory. In one embodiment, the camera is provided by Opteon, Inc., part number CA0010B025. This camera includes an electronic shuttering feature that is part of the so-called interline transfer charge coupled device (CCD) cameras. As known to one skilled in the art, interline CCD cameras include light-sensitive elements that accumulate charge as light falls on them and upon receiving a "trigger" pulse they reset to zero (black level) all at once. After an exposure interval, the light-sensitive cells dump their accumulations sideways into a "shifting" CCD, which will shift them out lengthwise to the digitizing system. The "shifting" CCD is protected from light. This has the effect of a shutter, since the amount of charge in the shielded shifting CCD cell is the amount of charge its neighboring unshielded cell accumulated between the trigger pulse and the end of the exposure interval. Electronic shuttering is preferred over mechanical shutters, which are relatively heavy, slow and wear out, and liquid crystal shutters, such as those disclosed in U.S. Pat. No. 5,260,779.

Figure 3:
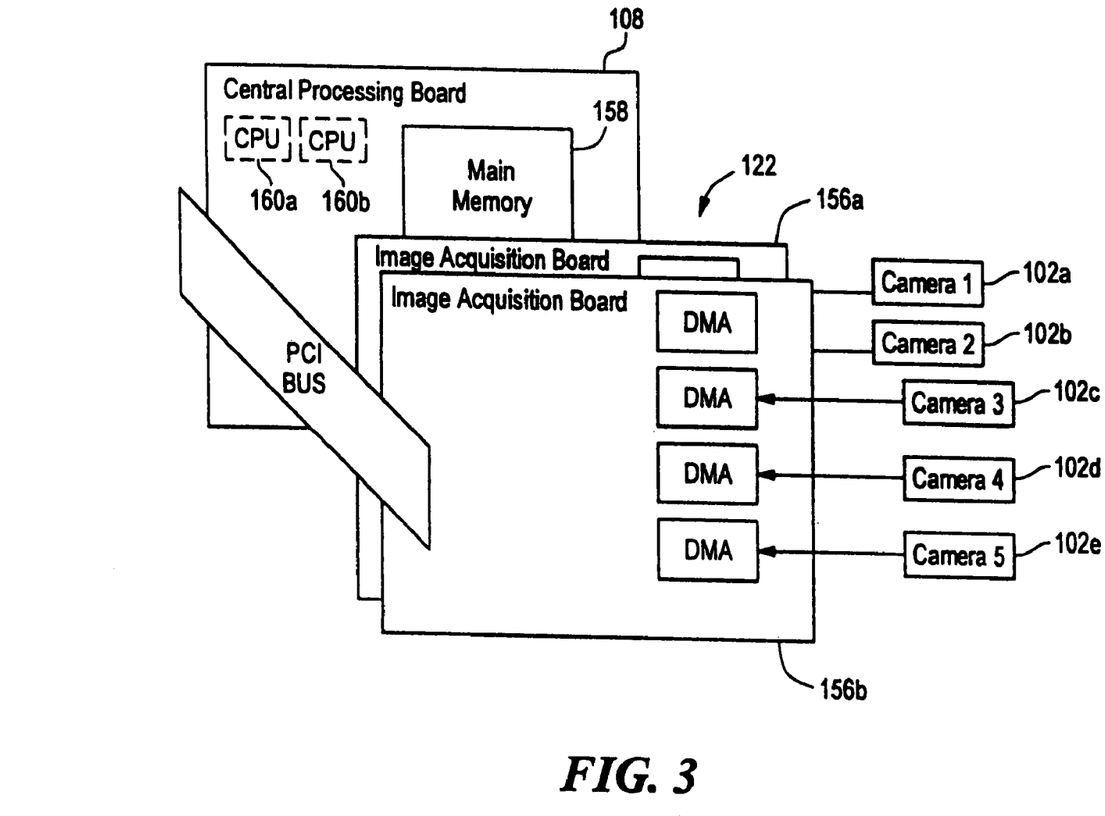
FIG. 3 is a block diagram of a frame grabber unit having direct memory access (DMA) channels that can form a part of the optical inspection system of FIG. 1.

FIG. 3 shows an exemplary embodiment of the frame grabber unit 122 of FIG. 1. The frame grabber unit 122 includes first and second image acquisition boards 156a,b, which can be provided as Depict Master boards (Part No. ELOCR4040PREN) made by Opteon, Inc, of Wellesley, Mass. The image acquisition boards 156 are coupled to the cameras 102 for receiving image data from the cameras. The image acquisition boards 156 utilize direct memory access (DMA) to send the image data to main computer memory 158, such as via a PCI bus, without processor intervention. In an exemplary embodiment, the main computer 108 controls the frame grabber unit 122 on stripe-by-stripe basis such that the image acquisition boards 156, under control of triggers stored in the trigger register 142 (FIG. 2), handle the transfers over the stripe. Thus, processing overhead for the main computer 108 can be devoted to image analysis rather than controlling data transfers. The main computer 108 can more efficiently process frames in memory, as well as handle interrupts concurrently with the image acquisition process.

This arrangement renders image data available to the main computer 108, e.g., two Pentium II processors 160a,b running Windows NT, immediately, and need not be transferred in a separate cycle. The processors 160a, 160b can directly access. i.e., from main memory, and process the images from five cameras on a opportunistic basis, i.e., as soon as a picture is ready the next available processor processes it. As used herein, direct access means that the main computer accesses the image data from main memory without the image data being transmitted over a bus external to a circuit on which the processors 160a,b are disposed.

In the exemplary five camera embodiment, the first and second cameras 102a, 102b are coupled to the first image acquisition board 156a and the third, fourth, and fifth cameras 102c, 102e are coupled to the second image acquisition board 156b. It is understood that although in this embodiment each image acquisition board 156a, 156b can handle four concurrent DMA channels (e.g. one channel for each of four cameras), image acquisition boards having any number of DMA channels can be used as long as all of the cameras utilized in the system can concurrently transfer their data directly to the main memory 158 in a DMA type process.

Figure 4:
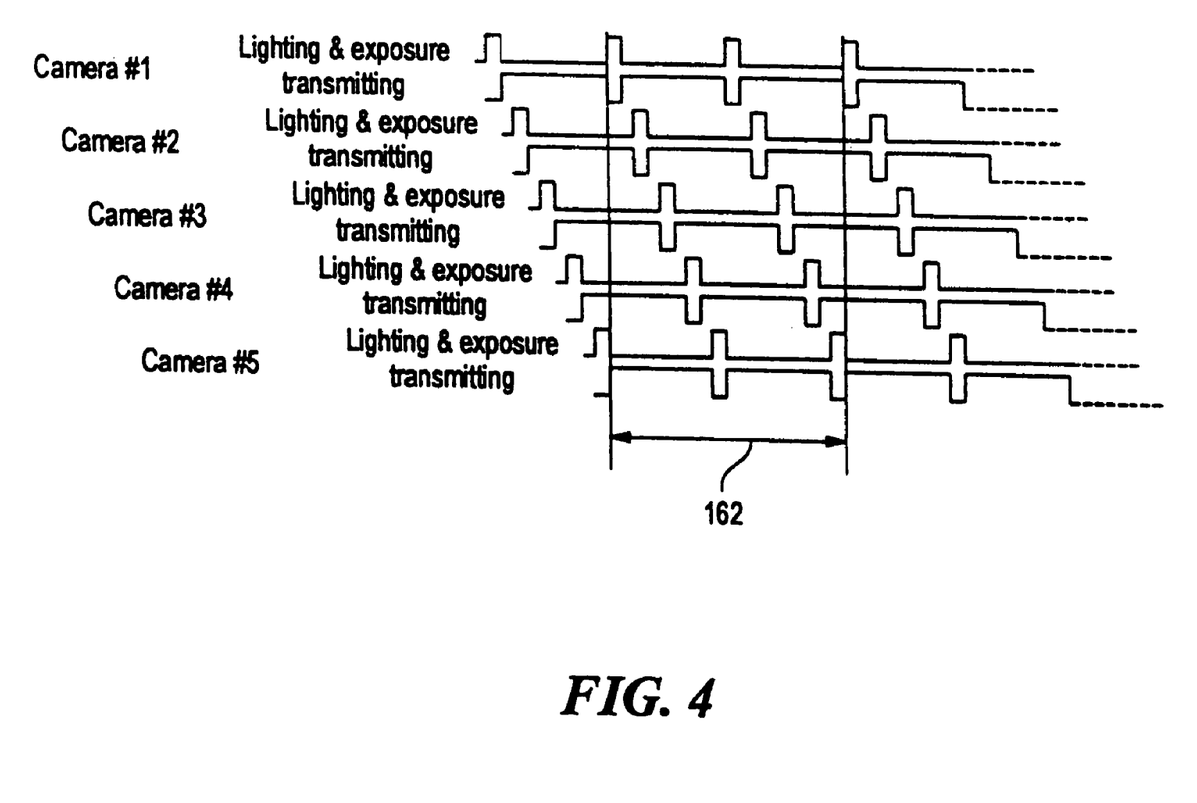
FIG. 4 is a timing diagram showing camera lighting/exposure and date transmission timing for cameras that can form a part of the optical inspection system of FIG. 4.

As shown in FIG. 4, each of the five cameras 102 (FIG. 3) transmits image data concurrently with the other. In the time 162 the cameras move one FOV, each camera can image a point on the board with multiple, e.g., two, lighting modes. This configuration provides full five by five image acquisition since each of the five cameras operates and transmits at full speed concurrently but staggered in phase. Thus, the full bandwidth of the cameras can be utilized.

Referring again to FIGS. 1–3, the five camera data streams flow into main memory 158 as the camera 102 moves along its path. The main memory 158 is at least of sufficient size to store all frames captured in one stripe, but can be increased to store additional stripe data. Processing by the main computer 108 begins as soon as there is at least one view to process, and continues until all views are processed. If one view takes more than one view acquisition time to process, the dome assembly or head 106 can still proceed, and the processing will either catch up during the next frame time, or can catch up at the end of the stripe while the head is stopping to reverse its motion, e.g., change direction.

The main memory 158 can store enough frames so that even if the main computer 108 cannot process the frames as quickly as they are acquired, the memory will not overflow during one sweep of the board under test. Because it takes time to mechanically move the camera 102 for a sweep, e.g., one pass over a stripe, the processors 160 can "catch-up" and finish processing the frames in memory between sweeps. That is, the time required for the cameras 102a–102e to reverse direction and be aligned with the next stripe provides additional processing time for the main computer 108 to complete analysis of the acquired images.

This arrangement provides a significant advantage over conventional systems that read image data from local memories on framegrabber boards, i.e., non-direct access. In this prior art approach, image data gets overwritten or flushed as soon as the camera transmits another frame. This image data must then be later re-acquired by sending the camera back to the point on the board to recapture the data corresponding to the lost image data.

Further advantages of the present invention are readily apparent over conventional optical image data acquisition configurations that handle multiple cameras by multiplexing data, i.e., not concurrently. That is, the image from one camera must be completely transmitted before another camera can transmit its image data. Thus, the full bandwidth of the cameras is not used so as to significantly reduce the efficiency of the system.

In operation, prior to beginning inspection of a circuit board, the main computer generates a view table. The view table is based on the images of the board that are to be analyzed. The function of the view table is described below. For a particular board, the main computer determines what points on the board are to be imaged and in which lighting modes. As known to one of ordinary skill in the art, a circuit board is fabricated and populated with components, such as by so-called pick and place systems. The components on the populated board are then soldered to the board. The identity, orientation, and position of the components, as well as the solder connection quality can be analyzed by the inspection system. In general, the main computer 108 utilizes a conventional macroexpansion facility whereby a CAD file can be combined with a library to produce an inspection program for a board having predetermined components, e.g. 0402 resistor, 0805 capacitor, quad flat pack (QFP)100 integrated circuit. The CAD file specifies the component location, the component name, and the component orientation. The macroexpansion facility reads the CAD file, and for each component in the CAD file, looks up the library element corresponding to its type. The windows, which are analyzed on a pixel basis, in the library element are then placed and rotated, assigned to proper camera and lighting mode combinations, and written into the view table or list. The main computer then associates a FOV with an area of the board to be viewed by one camera in one lighting mode. The list of windows is sorted into the view table so that all windows having a particular camera and lighting mode are placed into the view for that camera and that lighting mode.

Since each of the cameras 102*a*–102*e* operates asynchronously, the main computer 108 can organize the view table in a way that is better optimized to minimize the number of passes the camera head makes over the circuit board.

In the conventional system, the software organizes the view table into the "odd" camera fields and "even" camera fields so as to require multiple passes over any view in which the number of required lighting modes exceeds one per pair of cameras.

In contrast, the present intention allows the view table to be organized in five (where five cameras are used) completely independent parts. The lighting modes can be distributed five ways instead of two. Each camera may have two or more lighting modes at any point on the board during one pass.

Figure 5:
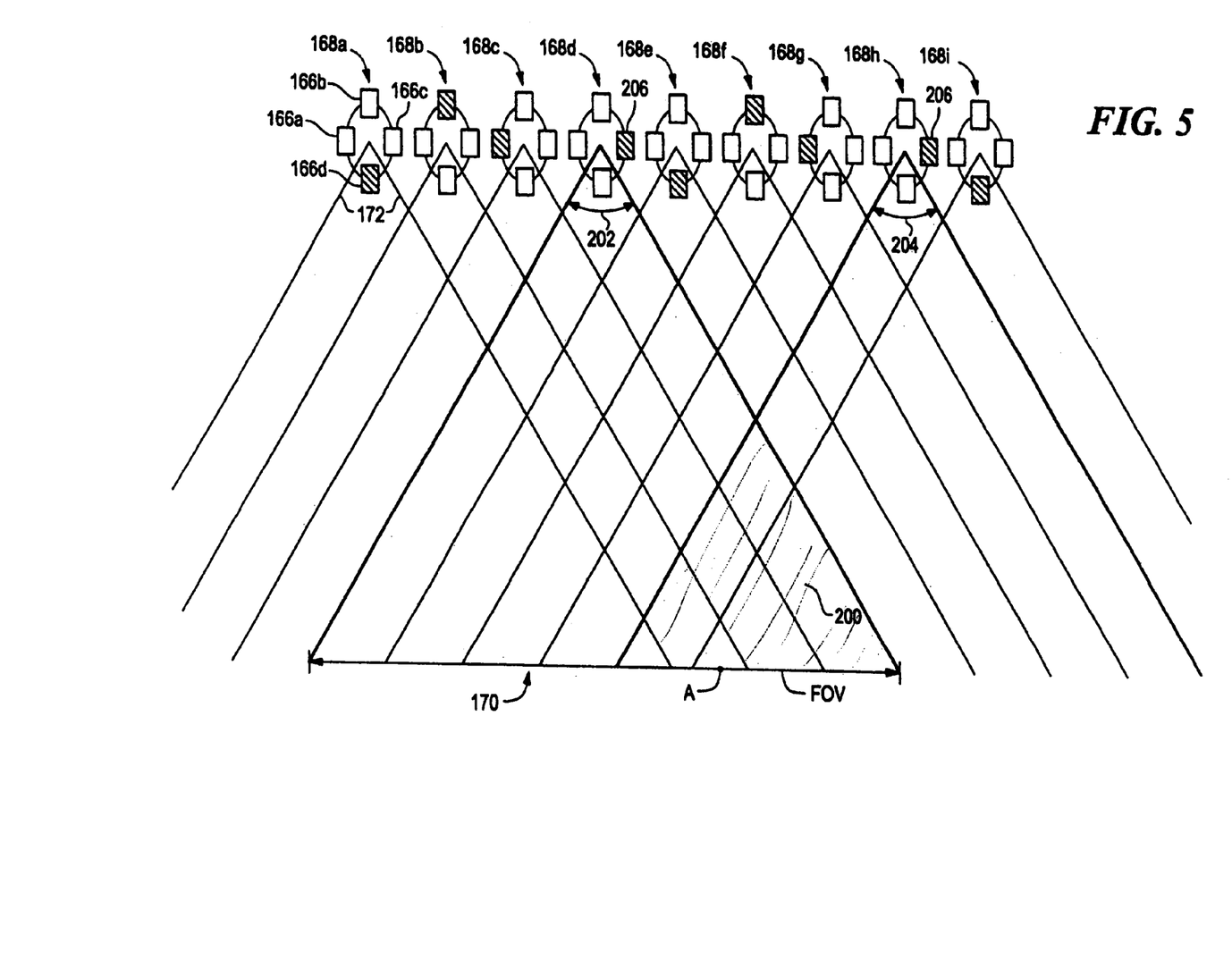
FIG. 5 is a pictorial representation of an exemplary camera trigger sequence during one half of a field of view for the optical inspection system of FIG. 1.
Figure 6:
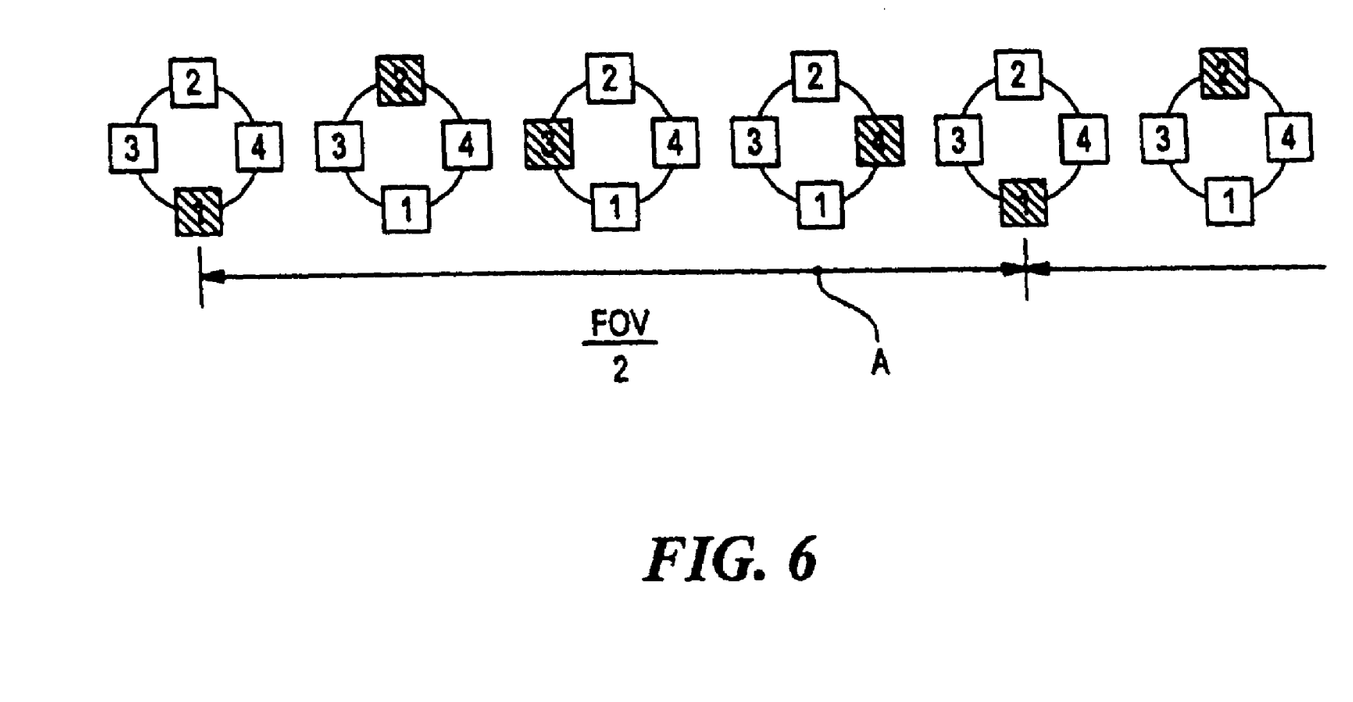
FIG. 6 is a pictorial representation of a how the cameras image a given location on an object under inspection by the optical inspection system of FIG. 1.

Referring now to FIGS. 5 and 6, a camera head 164 comprised of four cameras 166*a*–166*d* is shown in multiple positions 168*a*–168*i* as the camera head 164 moves across a printed circuit board surface 170. Each of the cameras 166*a*–166*d* has a field of view 172. As the camera head 164 moves, each point on the circuit board 170, such as point A in FIG. 5, can be imaged at least twice by each camera 166*a*–166*d*. It is understood, however, that a single point can be imaged more than two times in a single pass over the board, such as by slowing the speed of the camera head with respect to the stripe.

FIG. 5 shows a shaded overlap region 200 in which first and second views 202,204 by a given camera 206 image point A twice over a distance corresponding to one FOV. Thus, point A can be imaged in two different lighting modes by the same camera in one pass over the stripe in which point A resides.

In one embodiment, each camera 166*a*–166*d* acquires frames for an entire board in a predetermined number of lighting modes in a single pass over each location on the board. In cases where a different lighting mode is needed for each camera, this reduces inspection time over conventional systems since the system of the present invention allows a single point on the board to be imaged in multiple lighting modes in a single pass over the board, as described above. That is, the system provides multiple lighting modes per camera per field-of-view. For example, if a first FOV in a stripe needed only lighting modes A and B for camera X, and a different view in the stripe needed only lighting modes C and D for camera X, then all four lighting modes A–D could be accommodated in a single stripe for camera X.

The time required to inspect a board can be reduced by maximizing the camera bandwidth to the extent possible. In general, the camera can operate at a maximum number of frames per second. The head speed should be chosen such that each camera can acquire an image of a given point at least twice in a given FOV, e.g., once per FOV/2, where at least one point on the board requires two or more lighting modes.

In one embodiment, the camera is capable of up to about 60 frames per second. For a camera head speed of about 21 inches per second, as in conventional equipment, each camera may acquire a frame every 21/60 or 0.35 inches. At a field-of-view size of 0.7 inch, 0.35 inch is one half of the field of view distance. In this arrangement, a camera can take two complete images of a point each time it traverses one half of a 0.7 inch field of view. For a five camera system, the lighting system can be strobed 300 times per second —60 times per second for each of five cameras.

In contrast, conventional systems permit only one lighting mode per pass over the circuit board where the lighting system is strobed 60 times per second —30 times per second for the first pair of cameras and 30 times per second for the second pair of cameras.

The present system allows the head speed to be increased or decreased with relative ease to provide minimal inspection time based upon the requirements of a given inspection program. For example, a program can require three lighting modes for one or more points on the board. The head speed can be decreased to a level that allows three images of a given point on the board per FOV. In one pass over a stripe, the point can be imaged three times with the same camera in three different lighting modes. Thus, the board can be imaged in one pass at the cost of a slower head speed. Further, the head speed can be adjusted on a stripe-by-stripe basis depending upon the number of different lighting modes required over the stripe. Based on the requirements of a given inspection program, the main computer can determine the optimal head speed in view of the number of lighting modes associated with each point on the board to arrive at the fastest inspection time.

Furthermore, due to the asynchronous nature of the cameras, it is not necessary for the servo system which provides the camera head motion, to synchronize itself to the frame timing of the cameras. The cameras can be moved at the time appropriate to the needs of the motion system. It need never wait to mesh with the camera rhythm as in the conventional equipment.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An optical inspection system for inspecting an object, comprising:
    a plurality of cameras for imaging the object, each of the plurality of cameras being asynchronously triggerable;
    an illumination system for providing a plurality of lighting modes to illuminate the object for the plurality of cameras;

a frame grabber unit for transmitting image data from the plurality of cameras to a memory; and a main computer for controlling image acquisition of the object, wherein the plurality of cameras are adapted to obtain image data of the object based upon a plurality of fields of view of the object and a series of firing positions within each field of view, each of the firing positions having associated therewith at least one of the plurality of cameras and at least one of the plurality of lighting modes provided by the illumination system, wherein the optical image system is adapted to image a first one of the plurality of fields of view of the object with the at least one of the plurality of cameras in first and second ones of the plurality of lighting modes in a single pass.

2. The system according to claim 1, wherein image data provided by the plurality of cameras is sent to the memory concurrently.

3. The system according to claim 2, wherein the memory is main memory that is directly accessible by the main computer.

4. The system according to claim 1, wherein the plurality of cameras includes at least four cameras.

5. The system according to claim 1, wherein the object is a printed circuit board.

6. The system according to claim 1, wherein the frame grabber unit includes a plurality of DMA channels for storing data in the memory, which is directly accessible by the main computer.

7. The system according to claim 1, wherein the frame grabber unit includes at least one image acquisition board having a plurality of DMA channels for transmitting image data from at least two of the plurality of cameras to the memory, which is directly accessible by the main computer.

8. The system according to claim 1, further including a movable head assembly to which the plurality of cameras are secured and a position encoder for providing position information of the head assembly.

9. The system according to claim 8, wherein a velocity of the head assembly is adjustable to minimize inspection time of the object.

10. The system according to claim 1, further including an event memory for storing firing position data, camera trigger data, and a lighting mode for each of the plurality of firing positions.

11. An optical inspection system for inspecting an object, comprising:
a plurality of triggerable cameras for imaging the object;
an illumination system for providing a plurality of lighting modes to illuminate the object for the plurality of cameras;
a main computer coupled to the plurality of cameras and the illumination system; and
a frame grabber unit for receiving image data from the plurality of cameras, wherein the frame grabber unit includes at least one image acquisition board having a plurality of channels for transmitting image data from at least two of the plurality of cameras concurrently to main memory, which is directly accessible by the main computer, wherein each of the plurality of channels corresponds to a DMA channel
wherein the optical inspection system is adapted to image a first location on the object with a first one of the plurality of cameras in first and second ones of the plurality of lighting modes in a single pass over the first location.

12. The system according to claim 11, wherein main memory is adapted to store image data for more than one stripe.

13. The system according to claim 11, wherein the object is a circuit board.

14. A method of inspecting a circuit board, comprising:
selecting a speed for movement of a head assembly supporting a plurality of cameras with respect to the circuit board;
dividing the circuit board into field of views arranged in stripes, each field of view including a plurality of firing positions;
for each of the plurality of firing positions, selecting at least one of a plurality of asynchronously triggerable cameras and at least one of a plurality of lighting modes, wherein the optical inspection system is adapted to image a first location on the circuit board with the at least one of the plurality of cameras in first and second ones of the plurality of lighting modes in a single pass; and
transmitting image data from the plurality of cameras to memory.

15. The method according to claim 14, further including minimizing an inspection time of the circuit board from the head assembly speed, a number of lighting modes, and a number of passes over the circuit board required to image the circuit board.

16. The method according to claim 14, further including transmitting the image data to main memory that is directly accessible to a processor for analyzing the image data.

17. The method according to claim 16, further including transmitting the image data over a plurality of DMA channels.

18. The method according to claim 17, further including transmitting the image data from a plurality of cameras concurrently.

19. The method according to claim 14, further including imaging the circuit board in one pass over each stripe of the board, wherein at least one location on the board is imaged in at least two different lighting modes.

20. A method of manufacturing a circuit board, comprising:
fabricating a printed circuit board;
populating the circuit board with components;
soldering the components to the circuit board to provide a circuit board assembly; and
inspecting the circuit board assembly by
selecting a speed for movement of a head assembly supporting a plurality of cameras with respect to the circuit board,
dividing the circuit board into a plurality of field of views, each of which includes a plurality of firing positions;
for each of the plurality of firing positions, selecting at least one of a plurality of asynchronously triggerable cameras and at least one of a plurality of lighting modes, wherein the method of manufacturing is adapted to image a first location on the circuit board with the at least one of the plurality of cameras in first and second ones of the plurality of lightning modes in a single pass, and
transmitting image data from the plurality of cameras to memory.

* * * * *